United States Patent [19]

Kida et al.

[11] Patent Number: 5,011,766
[45] Date of Patent: Apr. 30, 1991

[54] SILVER HALIDE COLOR PHOTOGRAPHIC LIGHT-SENSITIVE MATERIAL

[75] Inventors: Shuji Kida, Hino; Hiroshi Kita; Shigeto Hirabayashi, both of Hachioji; Yutaka Kaneko, Sagamihara, all of Japan

[73] Assignee: Konica Corporation, Tokyo, Japan

[21] Appl. No.: 460,803

[22] Filed: Jan. 4, 1990

[30] Foreign Application Priority Data

Jan. 18, 1989 [JP] Japan .................................... 1-9272

[51] Int. Cl.$^5$ ............................................. G03C 1/08
[52] U.S. Cl. ................................. 430/558; 430/552; 430/543; 430/384
[58] Field of Search ............... 430/558, 552, 543, 384

[56] References Cited

U.S. PATENT DOCUMENTS 4,873,183 10/1989 Tachibana et al. ................. 430/558

FOREIGN PATENT DOCUMENTS 0236131 9/1987 European Pat. Off. ............ 430/558
299849 12/1987 Japan ................................... 430/558

Primary Examiner—Charles L. Bowers, Jr.
Assistant Examiner—T. Neville
Attorney, Agent, or Firm—Finnegan, Henderson, Farabow, Garrett and Dunner

[57] ABSTRACT

A silver halide color photographic light-sensitive material is disclosed, which is improved in the color forming efficiency, the color reproducibility and the resistivity of color image against heat and humidity. The photographic material comprises a silver halide emulsion layer which contains a pyrazoloazole type cyan coupler having a group represented by Formula I which is directly bonded to the azole ring of the pyrazoloazole coupler:

$$-(X=Y)_n-R_1 \qquad (I)$$

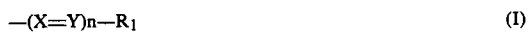

wherein X and Y each is a substituted or unsubstituted methine group or a nitrogen atom; $R_1$ is a hydrogen atom or a substituent; and n is an integer of 1 or 2, provided that two of Xs and two of Ys may be the same or different from each other when n is 2, and two of either X, Y and $R_1$ are allowed to be bonded each other to form a ring other than benzene ring.

7 Claims, No Drawings

SILVER HALIDE COLOR PHOTOGRAPHIC LIGHT-SENSITIVE MATERIAL

FIELD OF THE INVENTION

The present invention relates a silver-halide color photographic light-sensitive material, particularly relates to a silver-halide color photographic light-sensitive material containing a cyan dye forming coupler excellent in color forming efficiency.

BACKGROUND OF THE INVENTION

As a cyan color image forming coupler, compound of phenol type or naphtol type have been used conventionally.

However, cyan images formed from phenol type and naphtol type couplers have a serious problem in color reproducibility, i.e., the special absorption of the image has insufficient sharp cut off at the short wave length's end and an unnecessary absorption, or irregular absorption in green area. By them, the compensation of irregular absorption by masking technique must be applied in case of negative film. And in case of paper, there is no means to compensate so that color reproductivity becomes deteriorated.

Besides, dye image formed by phenol type or naphtol type couplers conventionally used have some problems in preservability. For example, a dye image formed from 2acylaminophenol cyan coupler described in U.S. Pat. Nos. 2,367,531 and 2,423,730 is inferior in heat resistivity and a dye image formed from 2,5-diacylaminophenol cyan coupler disclosed in U.S. Pat. Nos. 2,369,929 and 2,772,162 is inferior in light endurability and a dye image formed from 1-hydroxy-2-naphtamido cyan coupler is insufficient in both of heat and light endurability.

Besides, 2,5-diacylaminophenol cyan coupler described in U.S. Pat. No. 4,122,369 and Japanese Patent Publication to Public Inspection (hereinafter refer to Japanese Patent O.P.I. Publication Nos. 155538/1982 or 2,5-diacylaminophenol cyan coupler having a hydroxyl group in ballast part which is described in U.S. Pat. No. 3,880,661 can not attain satisfactory level in endurability against light or heat or in yellow stain so as to preserve its dye image for a long time. For the solving of these problems, in Japanese Patent O.P.I. Publication Nos. 199352/1988, 250649/1988 and 250650/1988, pyrazoloazole type cyan coupler were proposed.

But, in order to satisfy the absorbing wave length of dye to be formed, an electron attractive group and a hydrogen bond forming group are introduced to these coupler. As to these couplers, it is the most serious problem that coupling activity has been decreased remarkably so that color forming is extremely lowered compared with conventional phenol and naphtol type cyan coupler.

SUMMARY OF THE INVENTION

The first object of the invention is to provide silver-halide color photographic light-sensitive material (hereinafter simply refer to color photographic material) which is good in color forming property and which can form an image forming enough color density.

The second object of the invention is to provide a color photographic material which gives a clear cyan color image excellent in the spectral absorption and absorption is lowered in blue area and green area, namely, the edge of the absorption spectrum is sharply cut off.

The third object of the invention is to provide color photographic material which can form a cyan image which is inhabited in the variation of color phase caused by heat and humidity.

The above objects are accomplished by a silver-halide color photographic light-sensitive material comprising a silver halide emulsion layer containing a pyrazoloazole type coupler having a group represented by formula I which directly is binded to the azole ring of said pyrazoloazole coupler;

Formula I

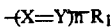

wherein X and Y each is a substituted or unsubstituted methine group or a nitrogen atom; $R_1$ is a hydrogen atom or a substituted group; n is an integer of 1 or 2, provided that two of Xs and two of Ys may be the same or different from each other when n is 2, and two of either X, Y, or $R_1$ are allowed be bonded each other to form a ring other than benzene ring.

DETAILED DESCRIPTION OF THE INVENTION

In the above-mentioned formula I, there is no limit in substituted group represented by $R_1$. Typically, such groups as an alkyl, aryl, anylino, acylamino, sulfonamido, alkylthio, arylthio, alkenyl, cycloalkyl group can be cited. Other than them, a halide atom, a nitro group, a hydroxyl group, a cychloalkenyl group, an alkynyl group, a heterocyclic group, a sulfonyl group, a sulfinyl group, a phosphonyl group, an acyl group, a carbamoyl group, a sulfamoyl group, a cyano group, an alkoxy group, an aryloxy group, a heterocyclic oxy group, a siloxy group, an acyloxy group, a carbamoyl oxy group, an amino group, an alkylamino group, an imido group, a ureido group, a sulfamoylamino group, an alkoxycarbonylamino group, an aryloxycarbonylamino group, an alkoxycarbonyl group, an aryloxy carbonyl group and a heterocyclic thio group can be used. Besides, a spiro compound residual group and bridged hydrocarbon compound residual group can also be cited.

As alkyl group represented by $R_1$, those having 1 through 32 carbon atoms are preferable, and they may be straight chain or branched chain.

As aryl group represented by $R_1$, a phenyl group is preferable.

As acylamino group represented by $R_1$, an alkylcarbonyl amino group, an arylcarbonylamino group are cited, for example..

As sulfonamido group represented by $R_1$, for example, an alkylsulfonylamino group, an arylsulfonylamino group are cited.

As alkyl component and aryl component in alkyl thio group and aryl thio group represented by $R_1$, alkyl groups and aryl groups cited as those groups represented by the above mentioned $R_1$ can be exemplified.

As alkenyl group represented by $R_1$, those having 2 to 32 carbons is preferable. As cycloalkyl group, those having 3 through 12, especially 5 to 7 carbons are preferable. The alkenyl groups may be straight chain or branched chain.

As cycloalkenyl group represented by $R_1$, those having 3 through 12 carbons, especially 5 to 7 are preferable.

Examples of the other groups represented by $R_1$ are given as follows;

Sulfonyl group : an alkyl sulfonyl group and an aryl sulfonyl group;

As sulfinyl group, alkyl sulphynyl group and arylsulphynyl group are used.

Phosphonyl group: an alkyl phosphnyl group, an alkoxyphosphonyl group, an aryloxyphosphonyl group, an arylphosphonyl group;

Acyl group: an alkyl carbonyl group and an aryl carbonyl group;

Carbamoyl group: an alkylcarbamoyl group and an arylcarbamoyl group;

Sulfamoyl group: an alkylsulphamoyl group and an aryl sulfamoyl group;

Acyloxy group: an alkylcarbonyloxy group and an arylcarbonyloxy group;

Carbamoyloxy group: alkylcarbamoyloxy group and arylcarbamoyloxy group;

Ureid group: an alkylureido group and arylureido group;

Sulfamoylamino group: an alkylsulfamoylamino group and an arylsulfamoylamino group;

Heterocyclic group: 5 to 7 member heterocyclic group such as 2-furyl group, 2-thienyl group, 2-pyrymizynyl group, 2-benzothiazoyl group;

Heterocyclic oxy group: preferably ones having 5 to 7 membering, such as, 3,4,5,6-tetrahydropyranyl-2-oxy group and 1-phenyltetrazole-5-oxy group;

Heterocyclic thio group: preferably ones having 5 to 7 member ring such as, 2-pyrizylthio group, 2-benzothiazoilthio group, and 2,4-diphenoxy-1,3,5-triazole-6-thio group;

Siloxy group: trimethylcyloxy group, triethylcyloxy group, and dimethylbutylcyloxy;

Imido group: succinimido group, 3-heptadecyl succiniimido group, phthalimido group and gultalimido group;

Spiro compound residual group spiro [3,3]heptan-1-yl;

Bridged hydrocarbon compound residual group; bicyclo [2.2.1]heptane-1-yl, tricyclo [3.3.1.1.3,7]decane-1-yl, 7,7-dimethyl-bicyclo[2.2.1]heptane-1-yl.

Among $R_1$, especially preferable are an aryl group, alkyl sulfonyl group, arylsulfonyl group, carbamoyl group, sulfamoyl group, acyl group, acylamino group, sulfon- amido group, alkoxy group, aryloxy group and alkoxycarbonyl group.

In the formula I, among circle structure formed by bonding two of either X, Y and $R_1$, preferable are rings of pyrydine, pyrimidine, pyridazine, pyrrole, pyrazole, imidazole, triazole, tetrazole, oxyazole, thiazole, furane, thiophene, oxadiazole and thiadiazole.

Preferable pyrazoloazole coupler in the present invention is a compound represented by the following formula II to VI.

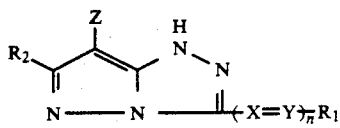

Formula II

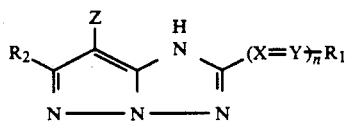

Formula III

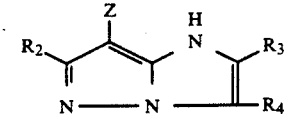

Formula IV

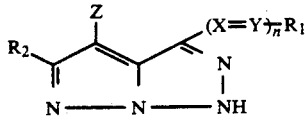

Formula V

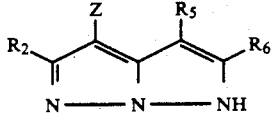

Formula VI

Wherein X, Y, R: and n are same as Formula I. $R_2$ is hydrogen atom or substituted group. Either one of $R_3$ or $R_4$ and either one of $R_5$ or $R_6$ are —(—X=Y—)-n—$R_1$, and the other is hydrogen atom or substitutent. Z is a hydrogen atom or a substituent capable of split off upon reaction with the oxidation product of a color developing agent.

As a substitutent each represented by $R_2$, $R_3$, $R_4$, $R_5$ and $R_6$, the same groups as $R_1$ in the formula I can be cited.

In formula II through VI, Z is preferable to be a halogen atom or such groups as bind with carbon atom in coupling position through oxygen atom, sulfon atom or nitrogen atom. It can be represented as the following formulas VII through XV.

 —$OR_7$      Formula [VII]

 —$SR_8$      Formula [VIII]

$R_7$ and $R_8$ is an alkyl group, such as, methyl, ethyl, propyl, butyl, amyl, octyl and dodecyl group or a phenyl group.

Alkyl group represented by $R_7$ and $R_8$ may have such substituents as followings. Namely, a halogen atom such atoms as fluorine, chlorin, and bromin; a hydroxyl group: a nitro group; a cyano group: a cyanoalkyl group such as, cyanomethyl group; a fluoroalkyl group such as trifluoromethyl group and octafluorobutyl group; an aryl group such as phenyl group and naphtyl group; an alkoxy group such as methoxy group, etoxy group, β-etoxyetoxy group, propyloxy group, t-butoxy group, pentyloxy group, i-pentyloxy group and dodecyloxy group; an aryloxy group such as phenoxy group and tryloxy group, a carboxyl group; an alkoxycarbonyl group such as ethoxycarbonyl group and dodecyloxycarbonyl group; an aryloxycarbonyl group such as phenoxycarbonyl group; an acyloxy group such as acetyloxy group, cyclohexylcarbonyloxy group and benzoyloxy group; alkylamino group such as ethylamino group, dimethylamino group, diethanolamino group, dodecylamino group and hexadecylamino group; an arylamino group such as anylino group and naphtylamino group;,an alkylcarbamoyl group such as, ethylcarbamoyl group, carboxyethylcarbamoyl group and dodecylcarbamoyl group; an arylcarbamoyl group such as phenylcarbamoyl group; an acylamino group such as methanamido group, dodecanamido group and benzamido group; an acyl group such as benzoyl group, pentafluorobenzoyl group and propylcarbonyl group; an alkylthio group such as methylthio group, propylthio group, octylthio group and dodecylthio group; an alkylsulfonyl group such as ethylsulfonyl group, octylsulfonyl group and dodecylsulfonyl group; an alkylsulfamoyl group such as pentylsulfamoyl group, dodecylsulphamoyl group, N-methylsulfamoyl group and N, N-dimethysulfamoyl group; an alkylsulfonamido group such as ethylsulfonamido group, dodecylsulfonamido group and p-dodecylphenylsulfonamido group; and an arylsulfonyl group such as phenylsulfonyl group can be cited.

Phenyl group represented by $R_7$ and $R_8$ can have the following substituted groups namely, an acyl amino group such as methanamido group, propanamido group, hexanamido group, dodecanamido group and benzamido; an alkylsulfonamido group such as methane sulfonamido group, propane sulfonamido group, hexanesulfonamido group and octanesulfon amido group; an arylsulfonamido group such as benzene sulfonamido group and naphtalenesulfon amido group; a carbamoyl group such as ethylcarbamoyl group, dodecylcarbamoyl group and phenylcarbamoyl group; sulfamoyl group such as N-ethylsulfamoyl group, N-octylsulfamoyl group, N, N-dimethylsulfamoyl group and phenylsulfamoyl group; an alkylureido group such as methylureido group and ethylureido group; an arylureido such as phenylureido group and naphtylureido group; an alkyl group such as methyl group, ethyl group, octyl group and dodecyl group, an alkoxy group such as methoxy group, ethoxy group, octyldodecyloxy group and butyloxy group; an amino group such as methyamino group, ethylamino group, butylamino group, octylamino group, dodecylamino group, dimethylamino group and anylino group; an alcoxycarbonyl group such as ethoxycarbonyl group, buthoxycarbonyl group, octyloxycarbonyl group and dodecyloxycarbonyl group or an aryloxycarbonyl group such as phenoxycarbonyl group.

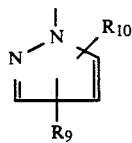

[IX]

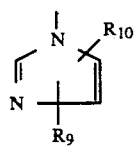

[X]

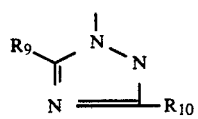

[XI]

$R_9$ and $R_{10}$ each is a hydrogen atom, a halide atom, an alkyl group, an alkoxy group, an aryl group, a heterocyclic group, a carbonic acid ester group, an amino group, an acyl-amino group, an alkylsulfonyl group, an arylsulphonyl group, an alkylsulfinyl group, an arylsulfinyl group, an alkylsulphoamido group, an aryl sulfonamido group and a carboxyl group. These groups may be the same or different from each other. Besides, the groups represented by $R_9$ and $R_{10}$ may form a ring.

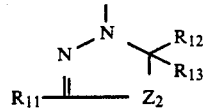

[XII]

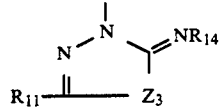

[XIII]

$Z_2$ and $Z_3$ each is a hetero atom or group such as —O—, —S—, —NR'—, in which R' is an alkyl group or an aryl group, $R_{11}$, $R_{12}$ and $R_{13}$ are the same atom as the above defined as $R_9$ and $R_{10}$.

$R_{14}$ is an alkyl group, an aryl group, an alkylcarbonyl group, an arylcarbonyl group, an alkylsulfonyl group or an arylsulfonyl group.

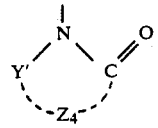

[XIV]

Y' is a hetero atom or group such as —NH—, —N=, —O— and —S; a sulfonyl group: a carbonyl group or carbon atom represented by

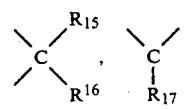

and $Z_4$ is a group of non-metal atoms necessary for forming a 5 to 6 member ring with the group of —Y'—N—CO—.

$R_{15}$, $R_{16}$ and $R_{17}$ each is a group the same as defined as $R_9$ and $R_{10}$. Besides, $R_{15}$, $R_{16}$ and $R_{17}$ allowed to combine to form a ring with a part of $Z_4$.

[XV]

$R_{18}$ and $R_{19}$ each is a hydrogen atom, an alkyl group, an aryl group, a substituted alkyl group, a substituted aryl group, an acyl group, a sulfonyl group, a hydroxyl group and a carboxyl group.

The spectral absorption of the cyann dye formed from a compound of the invention is shifted to long wavelength side, such fact may be caused by the conjugated system widened by introducing the group represented by formula I. Therefore, the compound of the present invention is not necessary to have a strong electron attractive substituent such as in conventional pyrazoroazol cyan coupler so that the electric density in the active site of the coupler may be raised and sufficient coupling ability can be obtained.

Hereunder, typical examples of the compound of the present invention are shown.

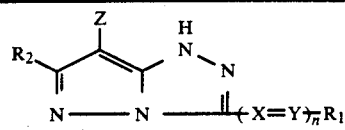

| No. | R₂ | $(X=Y)_nR_1$ | Z |
|---|---|---|---|
| 1 | $-NHCOCF_3$ | $-CH=CH_2$ | $-Cl$ |
| 2 | $-CH_2OCH_3$ | $-CH=CH-C_6H_4-NHCOCH(C_2H_5)O-C_6H_3(C_5H_{11}(t))_2$ | $-O-C_6H_5$ |
| 3 | $-CF_3$ | $-CH=CHSO_2-C_6H_4-OC_{12}H_{25}$ | $-S-C_6H_3(OC_4H_9)(C_8H_{17}(t))$ |
| 4 | $-C_6H_4-NO_2$ | $-C(CH_3)=CHCONHC_{14}H_{29}$ | $-N(pyrazolyl)$ |
| 5 | $-CH_3$ | $-CH=CHSO_2CH_2CH(C_6H_{13})(C_8H_{17})$ | $-Cl$ |
| 6 | $-C_6H_4-SO_2CH_3$ | $-CH=CHSO_2C_{16}H_{33}$ | $-Cl$ |
| 7 | $-SO_2C_{16}H_{33}$ | $-CH=CH-C_6H_5$ | $-N(piperidinyl)$ |
| 8 | $-SO_2CF_3$ | $-CH=C(CN)_2$ | $-NHSO_2-C_6H_4-OC_{12}H_{25}$ |
| 9 | $-NH-C_6H_4-Cl$ | $-CH=CHSO_2-C_6H_3(OC_4H_9)(C_8H_{17}(t))$ | $-SCH_2CH_2COOH$ |
| 10 | $-C_{15}H_{31}$ | $-(4-pyridyl)$ | $-Cl$ |
| 11 | $-OC_{15}H_{31}$ | $-(4-quinolyl)$ | $-OCH_2COOCH_3$ |

-continued
| No. | | —CH=CHOCOC₁₅H₃₁ | |
|---|---|---|---|
| 12 |  | | 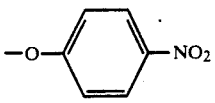 |
| 13 | 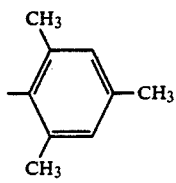 | 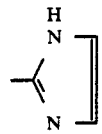 | 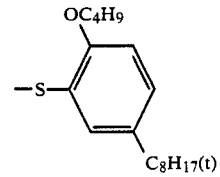 |
| 14 | —SO₂CH₃ | 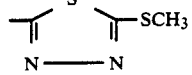 | —Cl |
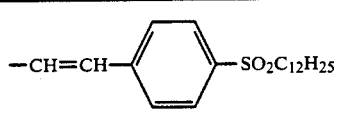
| No. | R₂ | —(X=Y)ₙR₁ | Z |
|---|---|---|---|
| 15 | —SO₂CH₃ | —CH=CH—⌬—SO₂C₁₂H₂₅ | —Cl |
| 16 | —SO₂CF₃ | —CH=CHSO₂C₁₈H₃₇ | 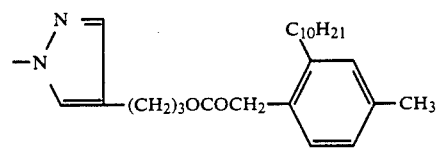 |
| 17 | —CF₃ | 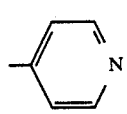 | 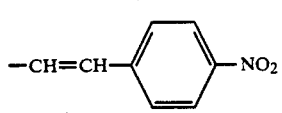 |
| 18 | —CF₃ | —CH=CH—⌬—NO₂ | —SC₁₆H₃₃ |
| 19 | 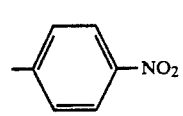 | —CH=CHCOOC₁₅H₃₁ | —Cl |
| 20 | —SO₂CH₃ | 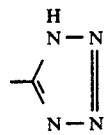 | 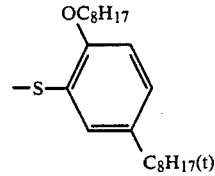 |
| 21 | —N⁺(CH₃)₃ | —CH=CHSO₂C₁₆H₃₃ | —Br |
| 22 | —CN | 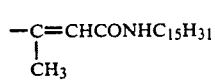 | 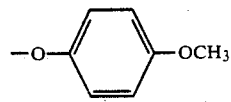 |

-continued

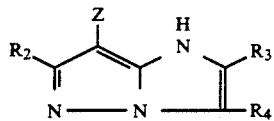

| No. | R₂ | R₃ | R₄ | Z |
|---|---|---|---|---|
| 23 | pentafluorophenyl | H | −CH=CH−C₆H₄−OC₁₂H₂₅ | −Cl |
| 24 | −SO₂CF₃ | 3,5-dimethyl-1,2,4-oxadiazol-yl (with O, N=N) | −CH₃ | −N(piperazine)N−C₁₅H₃₁ |
| 25 | −CN | 4-pyridyl | H | −OCH₂COOC₁₂H₂₅ |
| 26 | −OC₂H₅ | −CH=CHSO₂C₁₂H₂₅ | H | −SCH₂CH₂N(CH₃)₂ |
| 27 | −C₁₅H₃₁ | 3,4-dimethylpyridyl |  | −Cl |

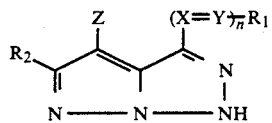

| No. | R₂ | −(X=Y)ₙ−R₁ | Z |
|---|---|---|---|
| 28 | −CH₃ | −CH=CHSO₂CH₂CH(C₆H₁₃)(C₈H₁₇) | −Cl |
| 29 | −SO₂CF₃ | −CH=CH−C₆H₅ | −S−[2-OC₄H₉-5-C₈H₁₇(t)-phenyl] |
| 30 | −SO₂C₁₆H₃₃ | methyl-tetrazol-yl | N-pyrazolyl |
| 31 | 4-methoxyphenyl | oxazol-2-yl | −O−[3-C₁₅H₃₁-phenyl] |

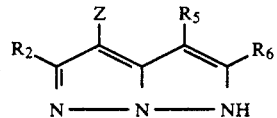

| No. | R₂ | R₅ | R₆ | Z |
|---|---|---|---|---|

-continued

| | | | | |
|---|---|---|---|---|
| 32 | $-SO_2C_8H_{17}$ | H | 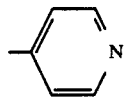 | $-Br$ |
| 33 | 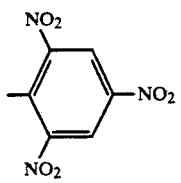 | 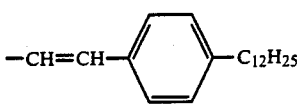 | H | $-Cl$ |
| 34 | $-CF_3$ | $-CH=CHSO_2C_{16}H_{33}$ | H | 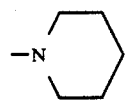 |
| 35 | 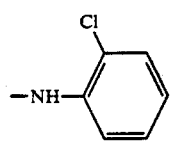 | 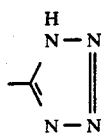 | $-C_{12}H_{25}$ | $-SCH_2CH_2COOH$ |
| 36 | $-SO_2CH_3$ | 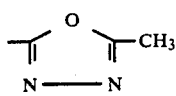 | H | 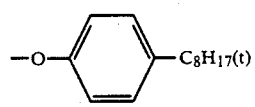 |

Hereunder, typical synthesizing example of compounds of the present invention is described.

EXAMPLE OF SYNTHETIZING 1

(Synthetizing of exemplified compound 5)

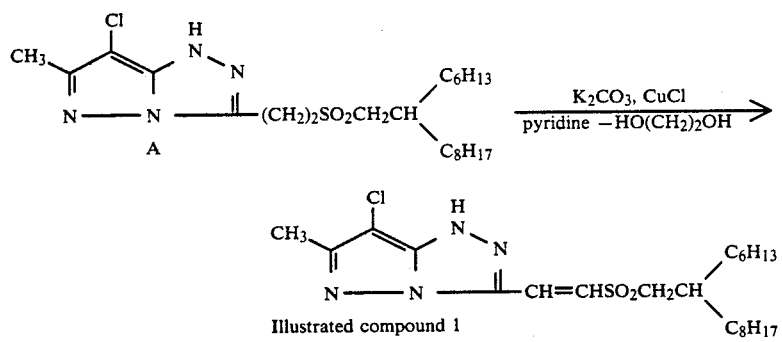

Fifty ml of ethylene glycol and 50 ml of pyridine are added to a mixture of 4.7 g of A, 3.46 g of potassium carbonate unhydride and 0.1 g of cuprous chloride. With introducing nitrogen, the mixture was heated and agitated for 2 hours at 80.C. To reacting solution, 200 ml of ethyl acetate and 200 ml of water were added. After the solution was acidulated by adding hydrochloric acid, the ethyl acetate layer was extracted. After washing the ethyl acetate layer for two times with water, it was vacuumed and concentrated. The resultant was applied to a chromathography with a colum using 250 g of silica gel, a mixture acetate ethyl: hexan=1:4 was used as a developing solvent. After the objective fraction was concentrated, it was re-crystalized from hexan to obtain 1.8 g of exemplified compound 1. Yield was 38%, and the melting point was from 95° C. to 97° C.

Mas spectol 471 (M++1).

NMR spectrol δ 7.9 (d 1H), δ 7.45 (d, 1H).
δ3.25(d, 2H), δ 2.35 (S, 3H),
δ1,9 (m, 1H),
δ1.1~1.4 (24H),
δ0.8 (m, 6H).

SYNTHESIZING EXAMPLE 2

(Synthetizing of exemplified compound 10)

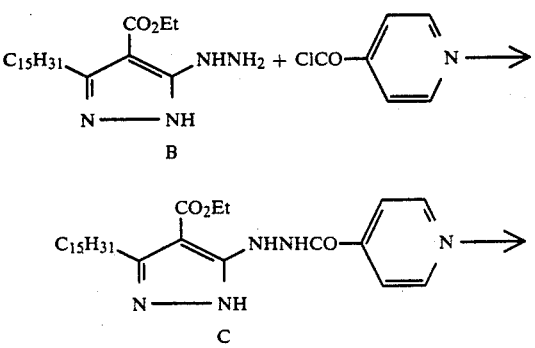

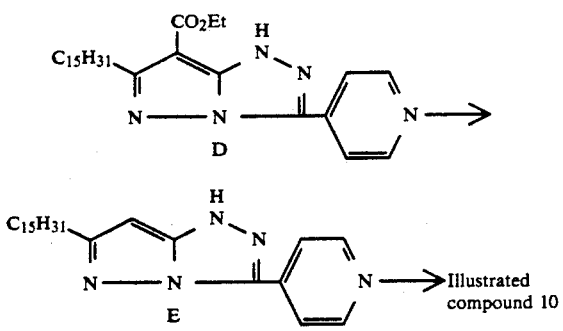

→ Illustrated compound 10

To 100 ml of methylene chloride solution containing 12.3 g of pyridine-4-carboxylic acid, 23.8 g of thionyl chloride was added gradually, then it was heated and reflexed for 2 hours. The reacting solution was concentrated under a vacuum. To the residue 50 ml of acetic acid was added to be solved. This is to be Solution A.

To 38.0 g of B, 1500 ml of ethyl acetate and 50 ml of aqueous solution containing 12.3 g of sodium acetate was added, to which Solution A was dropped. After heating and reflexing for two hours, water layer was eliminated, rematued ethyl acetate layer was washed with water and concentrated under a vacuum. To residue, ethyl acetate- hexan mixed solvent was added to be left, solid matter was separated. It was filtered and dried to yield 26.2 g of C.

Then, to 25 g of C, 250 ml of ethyl acetate and 9.2 g of thionyl chloride was added to be heated and reflexed for 2 hours. After chilling, 100 ml of water was added to extract ethyl acetate layer. To it, 100 ml aqueous solution containing 12.4 g of potassium hydrogen carbonate was added to be heated and reflected for 30 minutes. Water layer was eliminated, and after ethyl acetate layer was washed with water for two times, and concentrated under a vacuum.. The residue was refined by silica gel chlomathography to obtain 15.2 g of D.

Then, to 15 g of D, 7.5 ml of concentrated $H_2SO_4$ and 7.5 ml of water were added to be heated and reflected for 5 hours. The reacting solution was poured into the ice water. To it, ethyl acetate was added to be extracted. The extract was concentrated under a vacuum, then the residue was re-crystalized by ethyl acetate - acetonitryl mixed solvent to obtain 9.8 g of E.

Then, 9 g of E was solved to 100 ml of dimethylformamide, to which 3.2 g of N-chlorosuccinimido was added gradually. After agitating for 30 minutes, 300 ml of water, 300 ml of ethyl acetate and 5 ml of hydrochloric acid were added to the reacting solution. And the ethyl acetate layer was extracted to concentrate under a vacuum. The residue was re-crystaliized by ethyl acetate - hexane mixed solvent, to obtain 8.1 g of the exemplified compound 10.

The structure of the yielded compound was confirmed by NMR spectral and masspectral.

In silver halide photographic material in the present invention, it is preferable that cyan coupler of the present invention to be incorporated 0.1 to 100 mol% per mol of silver halide, more preferably 5 to 50 mol%. But it is possible to adjust appropriately according to the necessity.

Two or more couplers of the present invention can be used together. Besides, it can be used together with other kinds of cyan couplers. Couplers used in the present invention can be added to photographic material using various methods such as the solid dispersion method, the latex dispersion method and the oil in water type emulsifing and dispersion method. For example, in the oil in water type dispersion method, normally, hydrophobic additives such as couplers is disolved to high boiling point organic solvent such as tricresyl phosphate, dibutylphthalate and so on whose boiling point is not less than 150° C. to which low boiling point and/or water-soluble organic solvents such as ethyl acetate, butyl propionate may be added if necessary. The solution is dispersed with a surfactant into hydrophilic binder such as gelatin solution. The resulted dispersion is added into the objective hydrophilic colloidal layer.

When a color photographic light-sensitive material in the present invention is used as that for full color light-sensitive material, yellow coupler, magenta coupler are used other than cyan coupler in the present invention. As for yellow coupler and magenta coupler, there is no limitation and conventional types can be used.

As yellow coupler, for example, an acylacetoanilide type couplers can be used, to which benzoylacetoanilide type and pyvaloylacetoanilide type compound are included.

As a magenta coupler, for example, 5-pyrazolon type couplers, pyrazolobenzimidazole type couplers, pyrazolotriazole type couplers, open chain acylacetonitryl type couplers can be used.

For a color photographic light-sensitive material, water soluble dye may be contained to hydrophilic colloidal layer as a filter dye or as irradiation preventing or some other purposes.

To color photographic light-sensitive material in the present invention, various additives for photographic use such as an anti-foggant, development accelerating agent, a development inhibiting agent, bleaching accelerating agent, stabilizer, ultra-violet absorber, color-stain preventing agent, optical whitening agent, color image anti-fading agent, antistatic agent, hardener, surfactant, plasticizer and lubricant can be contained. As to these additives research disclosure Journal No. 17643 can be refered.

Besides, a competitive coupler and a compound capable of releasing a photographically useful fragment such the processing promoting agent, bleaching promoting agent, processor, silverhalide solvent, color conditioner, hardener, foggant, antifoggant, chemical sensitizer, spectral sensitizer and desensitizer upon coupling reaction with the oxidation product of a color developing agent can be used in the color photographic material of the invention.

As the support of the color photographic material of the present invention, for example, a baryta coated paper, polyethylene laminated paper; polypropyrene synthesic paper; glss plate; cellulose acetate film; cellulose nitrate film; polyester film such as polyethyleneterephthalate film; polyamide film; polycarbonate film; and polystyrene film may be used. In case of transparent support, reflecting layer may be used provided.

These support can be selected appropriately according to the purpose of photographic material.

For the coating of emulsion layer or other layers in the present invention, for example, dipping coating method, air doctor coating method, curtain coating method, and hopper coating method can be used. Besides, simultanuous coating method two or more layers described in U.S. Pat. Nos. 2,781,791 and 2,941,898 can also be used.

In the present invention, arrangement of each silver halide emulsion layer may arbitrarily be decided, but it is preferable to arrange blue sensitive emulsion layer, green sensitive emulsion layer and red sensitive emulsion layer in order from the support's side.

In the light-sensitive material of the present invention, it is optional to provide appropriate thickness of a intermediate layer according to the purpose. Besides, various kind of layers for example, filter layer, anti-carling layer, protective layer and anti-halation layer can be combine appropriately as a component layers. As such component layers, hydrophilic colloid can be used as binder, and gelatin may be used preferably. Besides, to such layer various photographic additives illustrated by the above-mentioned emulsion can be added.

There is no limitation in processing method for photographic light-sensitive material of the present invention. Various processing method which are known widely can be applied. For example, as the typical method; after color development, bleaching and fixing processes are applied if necessary, washing and/or stabilizing are done; after color development, bleaching and fixing are separately applied, and if necessary, washing and/or stabilizing processing is done. The color photographic material of the invention is suitable for being processed rapidly in the color developing, bleaching and fixing and washing stabilizing process.

EXAMPLE

Hereunder, practical examples of the invention is described, but the embodiment of the present invention cannot be limited to them. Example-1

Here, the present invention was applied to the color paper.

Namely, on a paper support whose both surface have been laminated by polyethylene, the following each layer was coated in order from the support side. Silver halide color photographic light-sensitive material No.1~18 were prepared:.

Layer 1 . . . a layer containing 1.2g/m$^2$ of gelatin, 0.32g/m$^2$ (in terms of silver hereunder same), of blue sensitive silver chlorobromide emulsion, containing 99.3 mol% of silver chloride: and 0.80 g/m$^2$ of yellow coupler (Y-1) disolved in 0.50 g/m$^2$ of dioctylphthalate.

Layer 2 . . . an intermediate layer containing 0.70g/m$^2$ of gelatin; 30mg/m$^2$ and 20 mg/m$^2$ of anti-iradiation dyes AI-1,and AI-2, respectively.

Layer 3 . . . A layer containing 1.25 g/m$^2$ of gelatin, 0.25g/m$^2$ of green sensitive silver chlorobromide emulsion containing 99.5 mol% of silver chloride; and 0.74g/m$^2$ of magenta coupler (M-1) disolved in 0.30g/m$^2$ of dioctylphthalate.

Layer 4 . . . An intermediate layer containing 1.20 g/m$^2$ of gelatin.

Layer 5 . . . A layer containing 1.20g/m$^2$ of gelatin, 0.30g/m$^2$ of red sensitive silver chlorobromide emulsion, containing 99.7 mol% of silver chloride: and 0.9 mili mol/m$^2$ of cyan coupler disolved in 0.45g/m$^2$ dioctyl phthalate illustrated in Table-1.

Layer 6 . . . A layer containing 1.00 g/m$^2$ of gelatin and 0.30 g/m$^2$ of ultra violet absorber (UV-1) which has been disolved in 0.20g/m$^2$ of dioctylphthalate.

Layer 7 . . . A layer containing 0.50 g/m$^2$ of gelatin.

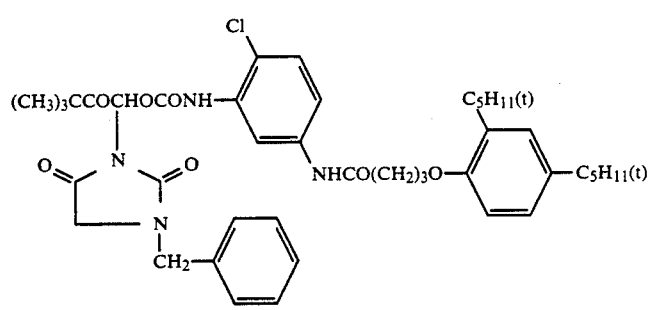

Y-1

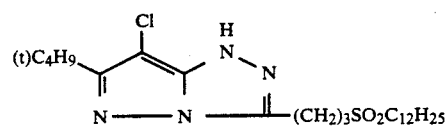

M-1

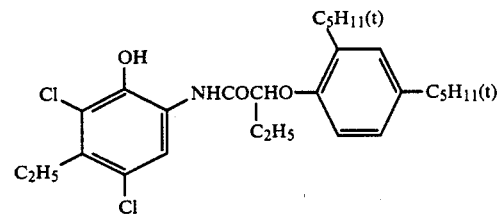

CC-1

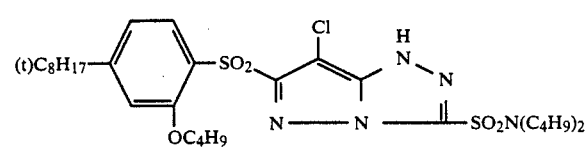

CC-2

-continued

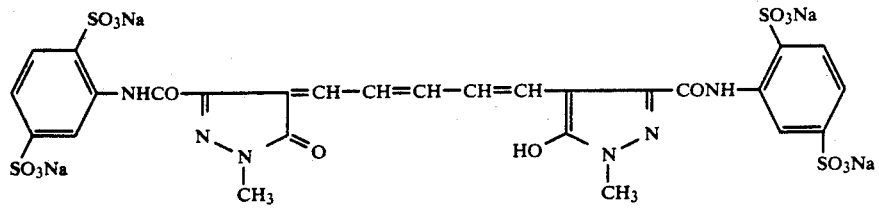
AI-1

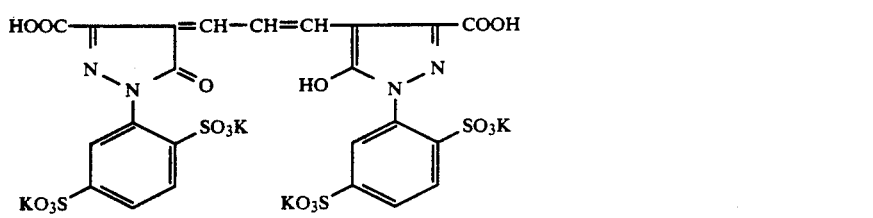
AI-2

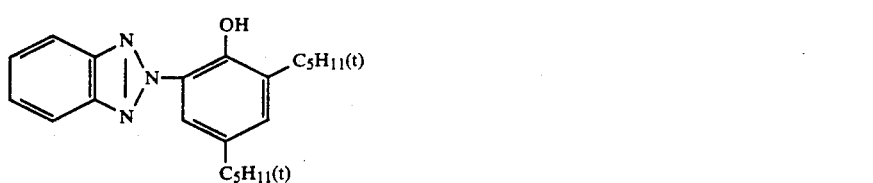
UV-1

As a hardener, sodium 2,4-dichloro-6-hydroxy-s-triazine was added to the second layer, the fourth layer and the seventh layer so that they are 0.017 g per 1 g of gelatin.

Thus, prepared sample were each exposured to light through an optical wedge with using the sensitometer KS-7 type (Manufactured by KONICA CORPORATION), then they are processed according to the following color processing procedure. Then, the maximum density (Dmax) of the red sensitive layer was measured by red light using an optical densitometer (PDA-65 type, manufactured by KONICA CORPORATION).

| | Temperature | Time |
|---|---|---|
| Color developing | 34.7 ± 0.3° C. | 45 seconds |
| Bleaching and fixing | 34.7 ± 0.5° C. | 45 seconds |
| Stabilizing | 30~34° C. | 90 seconds |
| Drying | 60~80° C. | 60 seconds |

| Color developer | |
|---|---|
| Pure water | 800 ml |
| triethanolamin | 8 g |
| N,N-diethylhydroxylamin | 5 g |
| Potassium chloride | 2 g |
| N-ethyl-N-β-methanesulfonamidoethyl-3-methyl-4-aminoaniline.sulfate | 5 g |
| Sodium tetrapolyphosphate | 2 g |
| Potassium carbonate | 30 g |
| Potassium sulfite | 0.2 g |
| fluorescence whitening agent (4,4'-diaminostylbendisulfonic acid derivative) | 1 g |

Add pure water to make 1 liter in total to adjust to pH 10.2.

| Bleach-fixing solution | |
|---|---|
| Ferric ammonium ethylenediaminetetraacetate di hydride | 60 g |
| Ethylene diamine tetraacetic acid | 3 g |
| Ammonium thiosulfate (70% solution) | 100 ml |
| Ammonium sulfite (40% solution) | 27.5 ml |

Add water to make 1 liter in total, then adjust its pH to 5.7 by potassium carbonate or gracical acetic acid.

| Stabilizer solution | |
|---|---|
| 5-chloro-2-methyl-4-isothiazoline-3-on | 1 g |
| 1-hydroxyethlidene-1,1-diphosphoric acid | 2 g |

Add water to make 1 liter, and adjust to pH=7.0 by potassium hydroxide or sulfuric acid.

Besides, as for the above samples No.1~18, color reproducibility was estimated, by the following procedure.

At first, Color Checker manufactured by Macbesth Co., Ltd. was photographed with using color negative film KONICA color GX-100: manufactured by KONICA and a camera, KONICA FT-1 Motor: manufactured by KONICA CORPORATION. In succession, the film was subjected to color negative processing (CNK-4: KONICA CORPORATION). Thus obtained negative image was printed by Konica Color Printer P-2000 to the above-mentioned sample No. 1 through 18 in 82 mm×117 mm size, to get prints as processed same as the above-mentioned example-1. The condition in printing was set sample by sample so that the gray color on the color checker is reproduced gray on the print.

As for gained prints, reproducibility of color and/or black portion were visually evaluated.

The results was shown in Table 1.

| Sample No. | Cyan coupler | Maximum density | Color reproductivity | | | Black reproducibility | NOTE |
| --- | --- | --- | --- | --- | --- | --- | --- |
| | | | Cyan | Blue | Green | | |
| 1 | CC-1 | 2.67 | P | P | P | GOOD | COMPARATIVE |
| 2 | CC-2 | 1.73 | G | G | G | INSUFFICIENT | COMPARATIVE |
| 3 | EX-1 | 2.61 | E | E | E | GOOD | THE INVENTIVE |
| 4 | EX-2 | 2.48 | E | E | E | GOOD | THE INVENTIVE |
| 5 | EX-3 | 2.52 | E | E | E | GOOD | THE INVENTIVE |
| 6 | EX-4 | 2.54 | E | E | E | GOOD | THE INVENTIVE |
| 7 | EX-5 | 2.62 | E | E | E | GOOD | THE INVENTIVE |
| 8 | EX-7 | 2.55 | E | E | E | GOOD | THE INVENTIVE |
| 9 | EX-8 | 2.59 | E | E | E | GOOD | THE INVENTIVE |
| 10 | EX-9 | 2.56 | E | E | E | GOOD | THE INVENTIVE |
| 11 | EX-10 | 2.61 | E | E | E | GOOD | THE INVENTIVE |
| 12 | EX-12 | 2.54 | E | E | E | GOOD | THE INVENTIVE |
| 13 | EX-14 | 2.53 | E | E | E | GOOD | THE INVENTIVE |
| 14 | EX-15 | 2.53 | E | E | E | GOOD | THE INVENTIVE |
| 15 | EX-18 | 2.54 | E | E | E | GOOD | THE INVENTIVE |
| 16 | EX-23 | 2.49 | E | E | E | GOOD | THE INVENTIVE |
| 17 | EX-29 | 2.52 | E | E | E | GOOD | THE INVENTIVE |
| 18 | EX-35 | 2.51 | E | E | E | GOOD | THE INVENTIVE |

P Color reproduction in the hue and saturation is insufficient
G Color reproduction in the hue and saturation is good
E Color reproduction in the hue and saturation is excellent As is clear from Table-1, Sample No.1 containing cyan coupler CC-1 which is not the present invention is good in color and high maximum density can be obtained. However, in color reproductibility, it is insufficient remarkably.

On the other hand, as for Sample No.2 containing cyan coupler CC-2 which is not the present invention, color reproductibility improves remarkably but as the maximum density is low, and the reproducibility in black portion is inferior.

To the contrary, as for Samples No.3 through 18 each containing cyan couplers of the present invention, the maximum density is high and both of reproductibilities color and black portion are excellent as a result of the couplers have high color forming efficiency.

What is claimed is:

1. A silver halide color photographic light-sensitive material comprising a red light sensitive silver halide emulsion layer containing a pyrazoloazole type cyan coupler having a group represented by Formula 1 which is directly bonded to the azole ring of said pyrazoloazole coupler:

$$-(X=Y)_n-R_1 \qquad (I)$$

wherein X and Y each is a substituted or unsubstituted methine group or a nitrogen atom; $R_1$ is a hydrogen atom or a substituent; and n is an integer of 1 or 2, provided that two of Xs and two of Ys may be the same or different from each other when n is 2, and two of either X, Y and $R_1$ are allowed to be bonded to each other to form a ring other than a benzene ring.

2. The material of claim 1, wherein said ring formed by bonding two of said X, Y and $R_1$ is a pyridine ring, a pyrimidine ring, a pyridazine ring, a pyrrole ring, a pyrazole ring imidazole ring, a triazole ring, a tetrazole ring, an oxazole ring, a thiazole ring, a furane ring, a thiophene ring, an oxadiazole ring or a thiadiazole ring.

3. The material of claim 1, wherein said group represented by $R_1$ is an aryl group, an alkylsulfonyl group, an arylsulfonyl group, a carbamoyl group, a sulfamoyl group, an acyl group, an acylamino group, a sulfonamido group, an alkoxy group, an aryloxy group or an alkoxycarbonyl group.

4. The material of claim 1, wherein said pyrazoloazole coupler is represented by Formulas II, III, IV, V or VI:

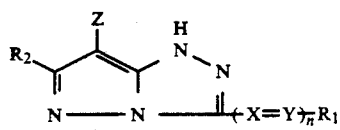 (II)

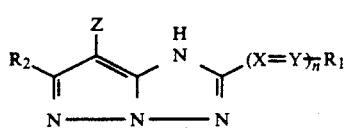 (III)

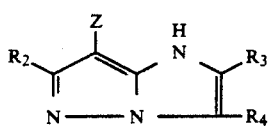 (IV)

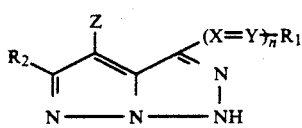 (V)

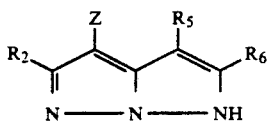 (VI)

wherein X, Y, $R_1$ and n are the same as X, Y, $R_1$ and n defined in Formula 1, respectively; $R_2$, is a hydrogen atom or a substituent; one of $R_3$ and $R_4$, and one of $R_5$ and $R_6$ are each the group of $-(X=Y)n-R_1$ and the other one of $R_3$ and $R_4$, and the other one of $R_5$ and $R_6$ are each a hydrogen atom or a substituent: and Z is a hydrogen atom or a substituent capable of splitting off upon reaction with the oxidation product of a color developing agent.

5. The material of claim 4, wherein said substituent represented by Z is a halogen atom or a group represented by Formula VII, VIII, IX, X, XI, XII, XIII, XIV or XV:

—OR$_7$ (VII)

—SR$_8$ (VIII)

wherein $R_7$ and $R_8$ are each an akyl group or a phenyl group;

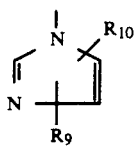 (IX)

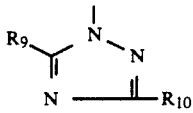 (X)

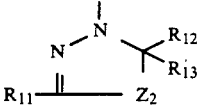 (XI)

wherein $R_9$ and $R_{10}$ are each a hydrogen atom, a halogen atom, an alkyl group, an alkoxy group, an aryl group, a heterocycic group, a carboxyl acid easter group, an amino group, an acylamino group, an alkylsulfonyl group, an arylsulfonyl group, an alkylsulfinyl group, an arylsulfinyl group, analkylsulfonamido group, an arylsulfonamido group or a carboxyl group, provided that the groups represented by $R_9$ and $R_{10}$ may be the same with or different from each other;

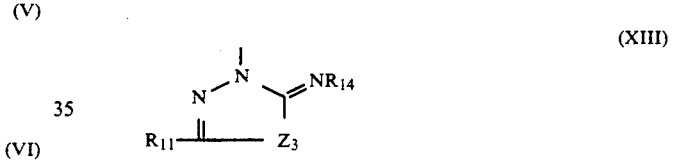 (XII)

(XIII)

wherein $Z_2$ and $Z_3$ are each an oxygen atom, a sulfur atom or a —NR' group, in which R' is an alkyl group or an aryl group; $R_{11}$, $R_{12}$ and $R_{13}$ are each the same as the group represented by $R_9$ defined in Formula IX and $R_{14}$ is an alkyl group, an aryl group, an alkylcarbonyl group, an arylcarbonyl group, an alkylsulfonyl group or an arylsulfonyl group;

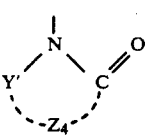 (XIV)

wherein Y' is an oxygen atom, a sulfur atom, a nitrogen atom an —NH—group, a sulfonyl group, a carbonyl group, a

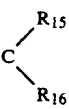

group or a C—$R_{17}$ group; $Z_4$ is a group of non-meta atoms necessary to form a five- or six-member ring incorporating the group of —Y'—N—CO—; $R_{15}$, $R_{16}$ and $R_{17}$ are each the same as the group $R_9$ defined in Formula IX, provided that each of $R_{15}$, $R_{16}$ and $R_{17}$ are allowed to form a ring incorporating a part of $Z_4$;

(XV)

wherein $R_{18}$ and $R_{19}$ are each a hydrogen atom, a substituted or unsubstituted alkyl group, a substituted or unsubstituted aryl group, an acyl group, a sulfonyl group, a hydroxyl group or a carboxyl group.

6. The material of claim 1, wherein said silver halide emulsion layer contains said cyan coupler in an amount of from 0.1 to 100 mol% of silver contained in said silver halide emulsion layer.

7. The material of claim 6, wherein said silver halide emulsion layer contains said cyan coupler in an amount of from 5 to 50 mol% of silver contained in said silver halide emulsion layer.

* * * * *

UNITED STATES PATENT AND TRADEMARK OFFICE
CERTIFICATE OF CORRECTION

PATENT NO. : 5,011,766
DATED : April 30, 1991
INVENTOR(S) : Shuji Kida et al.

It is certified that error appears in the above-identified patent and that said Letters Patent is hereby corrected as shown below:

Title Page:
In the Abstract, Line 16, after "bonded" insert --to--;

In the Abstract, Line 17, after "than" insert --a--;

Claim 1, Column 22, Line 54, after "formula" change "1" to --I--;

Claim 2, Column 23, Line 2, before "imidazole" insert -- , an --;

Claim 4, Column 23, Line 12, change "11I, 1V" to --III, IV--;

Claim 4, Column 23, Line 13, change "V1" to --VI--;

Claim 4, Column 23, Line 43, after "Formula" change "1" to --I--;

Claim 4, Column 23, Line 43, after "$R_2$" delete " , ";

UNITED STATES PATENT AND TRADEMARK OFFICE
CERTIFICATE OF CORRECTION

PATENT NO. : 5,011,766

DATED : April 30, 1991

INVENTOR(S) : Shuji Kida et al.

It is certified that error appears in the above-identified patent and that said Letters Patent is hereby corrected as shown below:

Claim 4, Column 23, Line 47, after "subsituent" change " : " to -- ; --;

Claim 5, Column 23, Line 60, change "akyl" to --alkyl--;

Claim 5, Column 24, Line 18, change "heterocycic" to --heterocyclic--;

Claim 5, Column 24, Line 18, change "easter" to --ester--;

Claim 5, Column 24, Line 21, change "analkysulfonamido" to --an alkylsulfonamido--;

Claim 5, Column 24, Line 54, after "atom" insert -- , --;

Claim 5, Column 24, Line 63, change "non-meta" to --non-metal--.

UNITED STATES PATENT AND TRADEMARK OFFICE
CERTIFICATE OF CORRECTION

PATENT NO. : 5,011,766

DATED : April 30, 1991

INVENTOR(S) : Shuji Kida et al.

It is certified that error appears in the above-identified patent and that said Letters Patent is hereby corrected as shown below:

Claim 5, Column 24, Line 63, change "non-meta" to --non-metal--.

Signed and Sealed this

Fifth Day of January, 1993

Attest:

DOUGLAS B. COMER

Attesting Officer

Acting Commissioner of Patents and Trademarks